United States Patent
Bafile et al.

(10) Patent No.: US 9,974,917 B2
(45) Date of Patent: May 22, 2018

(54) INLINE ADAPTER FOR A RESPIRATORY THERAPY DEVICE

(71) Applicant: KONINKLIJKE PHILIPS N.V., Eindhoven (NL)

(72) Inventors: Anthony Jon Bafile, Pittsburgh, PA (US); Mark Wayne Barclay, Saxonburg, PA (US)

(73) Assignee: Koninklijke Philips N.V., Eindhoven (NL)

( * ) Notice: Subject to any disclaimer, the term of this patent is extended or adjusted under 35 U.S.C. 154(b) by 379 days.

(21) Appl. No.: 14/646,740

(22) PCT Filed: Dec. 17, 2013

(86) PCT No.: PCT/IB2013/061037
§ 371 (c)(1),
(2) Date: May 22, 2015

(87) PCT Pub. No.: WO2014/097145
PCT Pub. Date: Jun. 26, 2014

(65) Prior Publication Data
US 2015/0306332 A1    Oct. 29, 2015

Related U.S. Application Data

(60) Provisional application No. 61/740,217, filed on Dec. 20, 2012.

(51) Int. Cl.
*A61M 16/08*    (2006.01)
*A61M 16/06*    (2006.01)
(Continued)

(52) U.S. Cl.
CPC .... *A61M 16/0816* (2013.01); *A61M 16/0057* (2013.01); *A61M 16/0666* (2013.01);
(Continued)

(58) Field of Classification Search
CPC .......... A61M 16/0816; A61M 16/0833; A61M 16/1095; A61M 16/0057; A61M 16/0666;
(Continued)

(56) References Cited

U.S. PATENT DOCUMENTS

| 2003/0059213 A1 | 3/2003 | Mackie et al. |
| 2008/0105257 A1 | 5/2008 | Klasek et al. |

(Continued)

FOREIGN PATENT DOCUMENTS

| DE | 19958296 C1 | 9/2001 |
| EP | 1127583 A2 | 8/2001 |

(Continued)

*Primary Examiner* — Andrew S Lo (57) ABSTRACT

An adapter apparatus (24, 80) for a respiratory therapy system (2) having a pressure generating device (4) and an electrical tube assembly (22) coupled to a patient interface device (8) includes a first end having a first port member (66, 94) structured to be fluidly coupled to the electrical tube assembly, a second end having a second port member (70, 88) structured to receive a flow of breathing gas generated by the pressure generating device, the adapter apparatus being structured to deliver the flow of breathing gas to the electrical tube assembly through the first port member, and a wire assembly having a first electrical connector (76, 104) structured to be electrically coupled to the electrical tube assembly and a second electrical connector structured to be electrically coupled to the pressure generating device in order to provide an electrical connection between the electrical tube assembly and the pressure generating device.

13 Claims, 7 Drawing Sheets

(51) Int. Cl.
*A61M 16/10* (2006.01)
*A61M 16/12* (2006.01)
*A61M 16/20* (2006.01)
*A61M 39/10* (2006.01)
*A61M 16/00* (2006.01)

(52) U.S. Cl.
CPC .... *A61M 16/0833* (2014.02); *A61M 16/0875* (2013.01); *A61M 16/1095* (2014.02); *A61M 16/0066* (2013.01); *A61M 16/06* (2013.01); *A61M 16/1055* (2013.01); *A61M 16/12* (2013.01); *A61M 16/208* (2013.01); *A61M 2039/1022* (2013.01); *A61M 2202/0208* (2013.01); *A61M 2205/36* (2013.01); *A61M 2205/50* (2013.01); *A61M 2205/7518* (2013.01)

(58) Field of Classification Search
CPC .......... A61M 16/0875; A61M 16/0066; A61M 16/06; A61M 16/1055; A61M 16/12; A61M 16/208; A61M 2039/1022; A61M 2202/0208; A61M 2205/36; A61M 2205/50; A61M 2205/7518

USPC ...................... 128/204.18, 202.27
See application file for complete search history.

(56) References Cited

U.S. PATENT DOCUMENTS

| | | |
|---|---|---|
| 2008/0142019 A1 | 6/2008 | Lewis et al. |
| 2009/0025723 A1 | 1/2009 | Baecke et al. |
| 2009/0260629 A1 | 10/2009 | Yee et al. |

FOREIGN PATENT DOCUMENTS

| | | |
|---|---|---|
| EP | 1277488 A1 | 1/2003 |
| WO | 2008076230 A2 | 6/2008 |
| WO | 2008105257 A1 | 9/2008 |
| WO | 2009022004 A2 | 2/2009 |
| WO | 2010022363 A1 | 2/2010 |
| WO | 2012031315 A1 | 3/2012 |
| WO | 2012160477 A1 | 11/2012 |
| WO | 2013012696 A1 | 1/2013 |
| WO | 2013151448 A2 | 10/2013 |

INLINE ADAPTER FOR A RESPIRATORY THERAPY DEVICE

CROSS-REFERENCE TO PRIOR APPLICATIONS

This application is the U.S. National Phase application under U.S.C. § 371 of International Application Serial No. PCT/IB2013/061037, filed on Dec. 17, 2013, which claims the benefit of U.S. Application Ser. No. 61/740,217, filed on Dec. 20, 2012. These applications are hereby incorporated by reference herein.

BACKGROUND OF THE INVENTION

1. Field of the Invention

The present invention pertains to systems for treating conditions, such as sleep disordered breathing, using positive airway pressure (PAP) therapy, and, in particular, to an inline adapter for a pressure support device that also allows for an electrical connection to be made between electrical (e.g., heated tubing) and the pressure support device.

2. Description of the Related Art

There are numerous situations where it is necessary or desirable to deliver a flow of breathing gas non-invasively to the airway of a patient, i.e., without intubating the patient or surgically inserting a tracheal tube into the patient's esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Some patients that use non-invasive ventilation and/or pressure support therapy devices have a need to add an inline accessory to the flow path of the device. Such accessories may include, for example and without limitation, oxygen enrichment adapters, pressure valves and bacteria filters. In addition, many patients are now using heated tubes in the flow path. Such heated tubes require an electrical connection to be made between a connector on the tube cuff and a connector near/on the outlet port of the ventilator or pressure support device. The requirement for such an electrical connection, however, makes it difficult to also use an inline accessory.

In the specific context of supplemental oxygen, in the prior art, in order to maintain heated tubing functionality while simultaneously receiving supplemental oxygen, the oxygen must be introduced to the patient at the mask side of the patient circuit, either directly into the mask or into an enrichment adapter provided between the mask and the main delivery conduit. This adds bulk to the mask and/or forces the patient to have additional tubing running to their face. This can reduce the comfort of the therapy experience, and thus may lease to decreased therapy compliance.

SUMMARY OF THE INVENTION

In one embodiment, an adapter apparatus for a respiratory therapy system having a pressure generating device and an electrical tube assembly, such as a heated tube assembly, coupled to a patient interface device. The adapter apparatus includes a first end having a first port member structured to be fluidly coupled to the electrical tube assembly, a second end having a second port member structured to receive a flow of breathing gas generated by the pressure generating device, the adapter apparatus being structured to deliver the flow of breathing gas to the electrical tube assembly through the first port member, and a wire assembly having a first electrical connector structured to be electrically coupled to the electrical tube assembly and a second electrical connector structured to be electrically coupled to the pressure generating device in order to provide an electrical connection between the electrical tube assembly and the pressure generating device.

In another embodiment, a respiratory therapy system is provided that includes a pressure generating device structured to generate a flow of breathing gas, a patient interface device, an electrical tube assembly coupled to the patient interface device, and an adapter apparatus as described above provided between the pressure generating device and the electrical tube assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
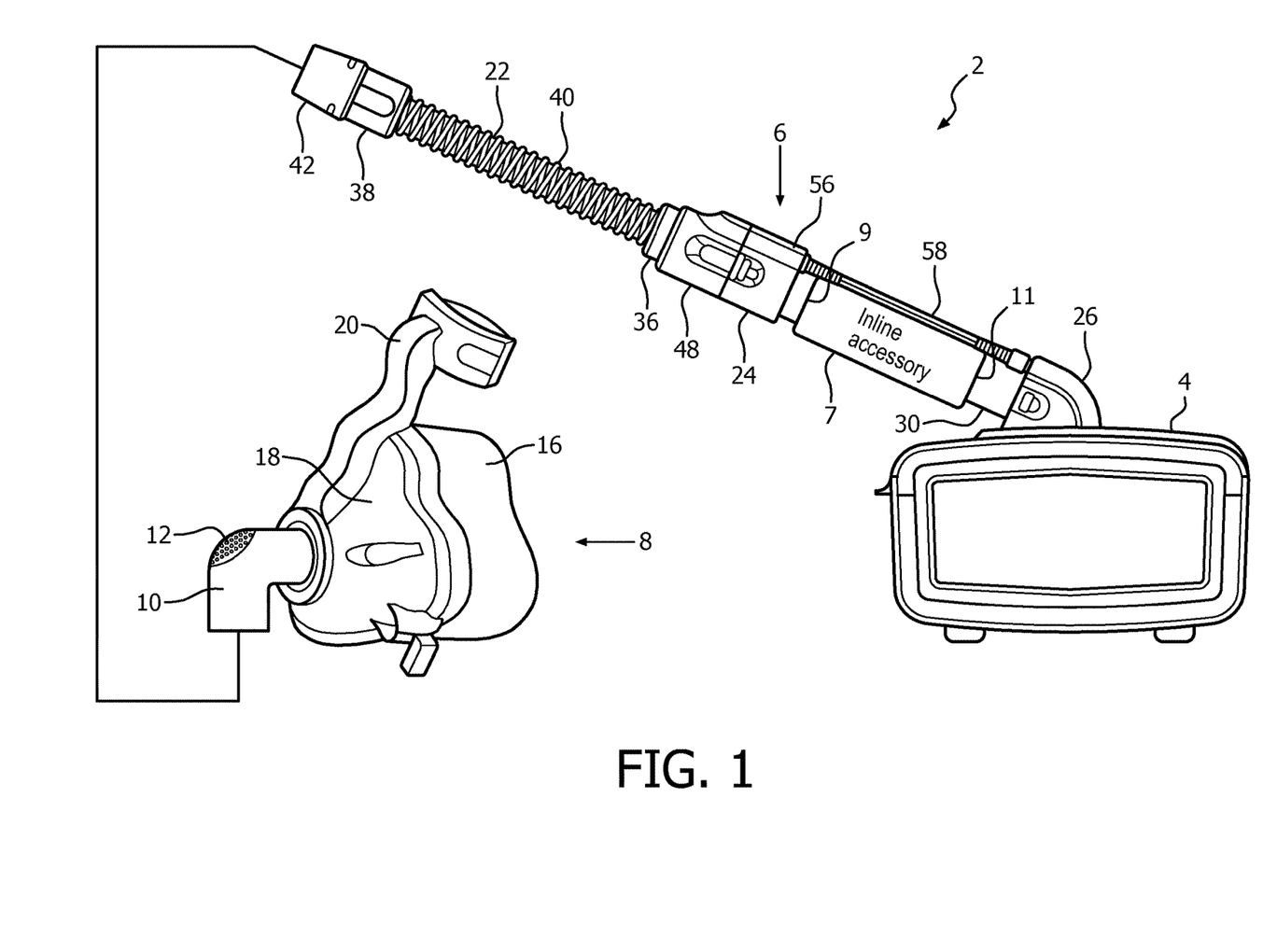
FIG. 1 is a schematic diagram of a system adapted to provide a regimen of respiratory therapy to a patient according to one exemplary embodiment of the invention.

A system 2 adapted to provide a regimen of respiratory therapy to a patient according to one exemplary embodiment of the invention is generally shown in FIG. 1. System 2 includes a pressure generating device 4, a delivery conduit assembly 6 (described in detail herein), and a patient interface device 8 including an elbow conduit 10 fluidly coupled to delivery conduit assembly 6.

Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit assembly 6 is structured to communicate the flow of breathing gas from pressure generating device 4 to patient interface device 8. As described in more detail herein, delivery conduit assembly 6 is a heated delivery assembly that also allows for inclusion of an inline accessory 7 (such as, without limitation, an oxygen enrichment adapter, a pressure valve, a bacteria filter, or any other suitable accessory device that may be used in the patient circuit of a respiratory therapy device), shown schematically in FIG. 1, in the flow path from pressure generating device 4 to patient interface device 8.

In the illustrated embodiment, patient interface 8 is a nasal/oral mask structured to cover the nose and mouth of the patient. However, any type of patient interface device 8, such as, without limitation, a nasal mask that covers the patient's nose, a nasal cushion having nasal prongs that are received within the patient's nares, or a full face mask that covers the patient's face, which facilitates the delivery of the flow of breathing gas to, and the removal of a flow of exhalation gas from, the airway of a patient may be used while remaining within the scope of the present invention. In the embodiment shown in FIG. 1, patient interface 8 includes a flexible cushion 16, a rigid or semi-rigid shell 18, and a forehead support 20. Straps (not shown) of a headgear component may be attached to shell 18 and forehead support 20 to secure patient interface device 8 to the patient's head. An opening in shell 18 to which elbow conduit 10 is coupled allows the flow of breathing gas from pressure generating device 4 to be communicated to an interior space defined by shell 18 and cushion 16, and then, to the airway of a patient. The opening in shell 18 also allows the flow of exhalation gas (from the airway of such a patient) to be communicated to an exhaust assembly 12 provided on elbow conduit 10.

As seen in FIG. 1, delivery conduit assembly 6 includes a heated tube assembly 22 that is directly fluidly coupled to a first end of an inline accessory adapter 24. Delivery conduit assembly 6 further includes inline accessory 7. In particular, as shown in FIG. 1, a first end of inline accessory 7 is directly fluidly coupled to a second end of inline accessory adapter 24, and a second end of inline accessory 7 is directly fluidly coupled to heated tube capable outlet port 26 of pressure generating device 4. In addition, as described in detail below, inline accessory adapter 24 is structured to enable the required electrical connection to be made between heated tube capable outlet port 26 and heated tube assembly 22 while simultaneously allowing inline accessory 7 to be inserted into the flow path.

Figure 2:
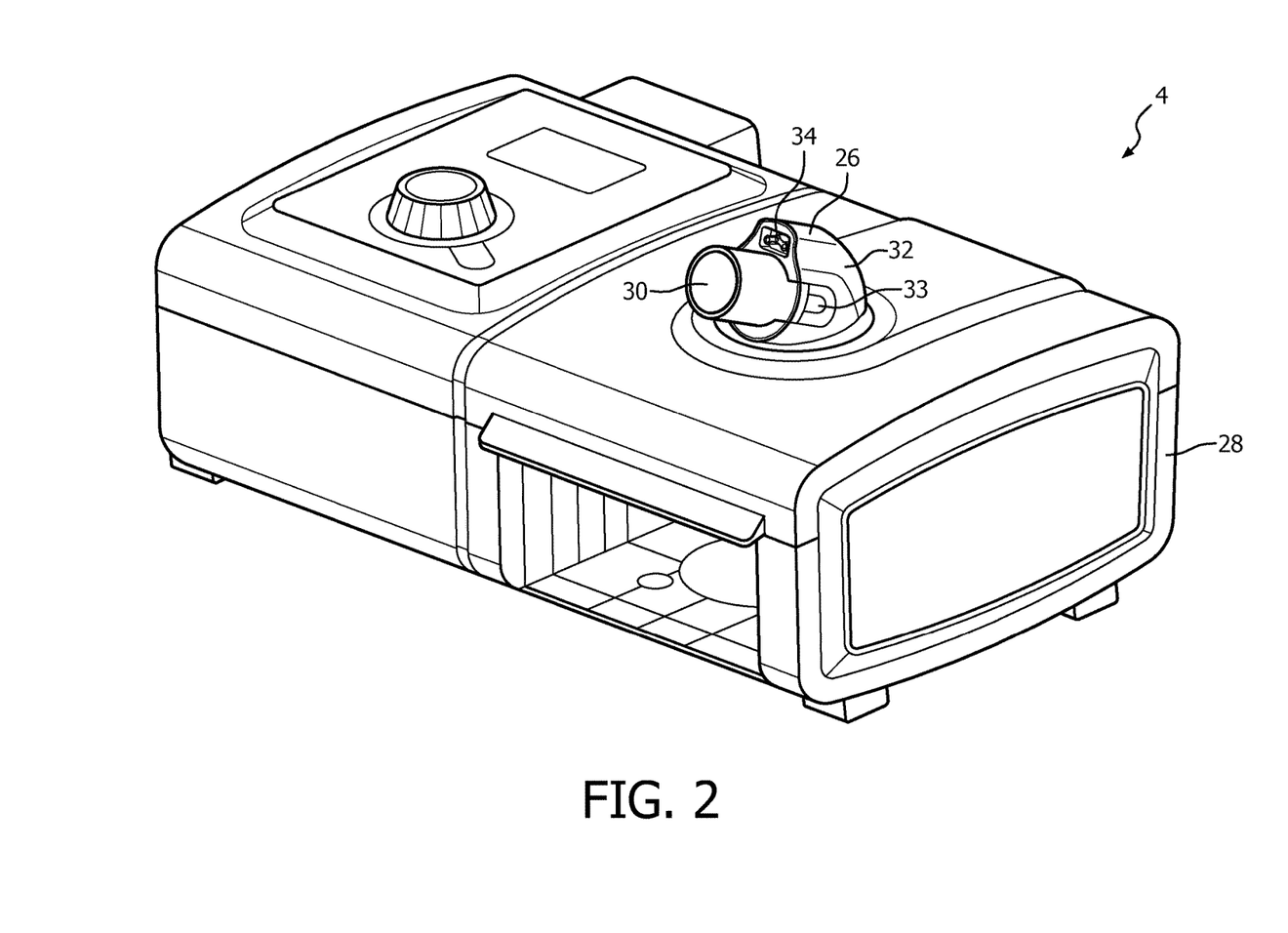
FIG. 2 is an isometric view of a pressure generating device forming a part of the system of FIG. 1 according to one exemplary embodiment of the invention.

FIG. 2 is an isometric view of pressure generating device 4 according to an exemplary embodiment. As seen in FIG. 2, pressure generating device 4 includes a main housing 28 which houses the main components of pressure generating device 4 (e.g., the flow generator (blower), valve(s), sensors, control electronics, etc.). Outlet port 26 is coupled to the flow generator and extends from the top side of main housing 28. Outlet port 26 includes a tubular port member 30, which in the illustrated embodiment is a standard male iso conical fitting, and a port housing 32 which houses an electrical connector 34. Electrical connector 34 is coupled to a power supply and/or other electronics (not shown) provided within main housing 28. Port housing 32 further includes slot members 33, the purpose of which is described elsewhere herein.

Figure 3:
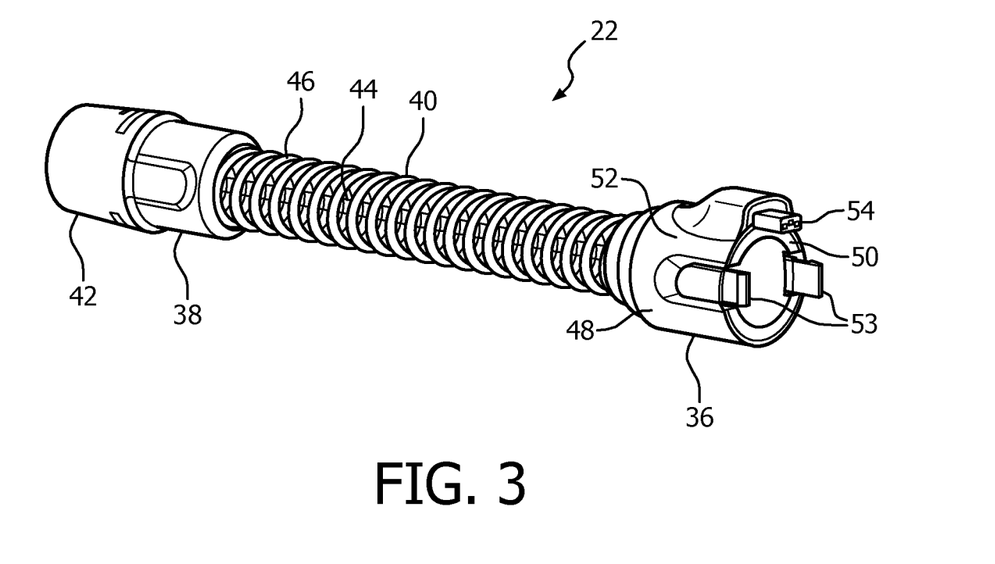
FIG. 3 is an isometric view of a heated tube assembly forming a part of the system of FIG. 1 according to one exemplary embodiment of the invention.

FIG. 3 is an isometric view of heated tube assembly 22 according to an exemplary embodiment. As seen in FIG. 3, heated tube assembly 22 includes a proximal end 36, a distal end 38, and heated tubing 40 provided between proximal end 36 and distal end 38. Distal end 38 is provided with a coupling member 42 structured to be fluidly coupled to elbow conduit 10, either directly or through intermediate tubing. Heated tubing 40 includes a central tubular member 44 surrounded by a helical heating element 46. Proximal end 36 is provided with a coupling member 48 that includes a tubular port member 50, which in the illustrated embodiment is a standard female iso conical fitting, and a port housing 52 which houses an electrical connector 54. Electrical connector 54 is operatively coupled to heating element 46 of heated tubing 40 to provide power and/or control signals thereto. Port housing 52 also includes tab members 53 which are structured to be received within slot members 33 when an inline accessory as described herein is not being used.

Figure 4:
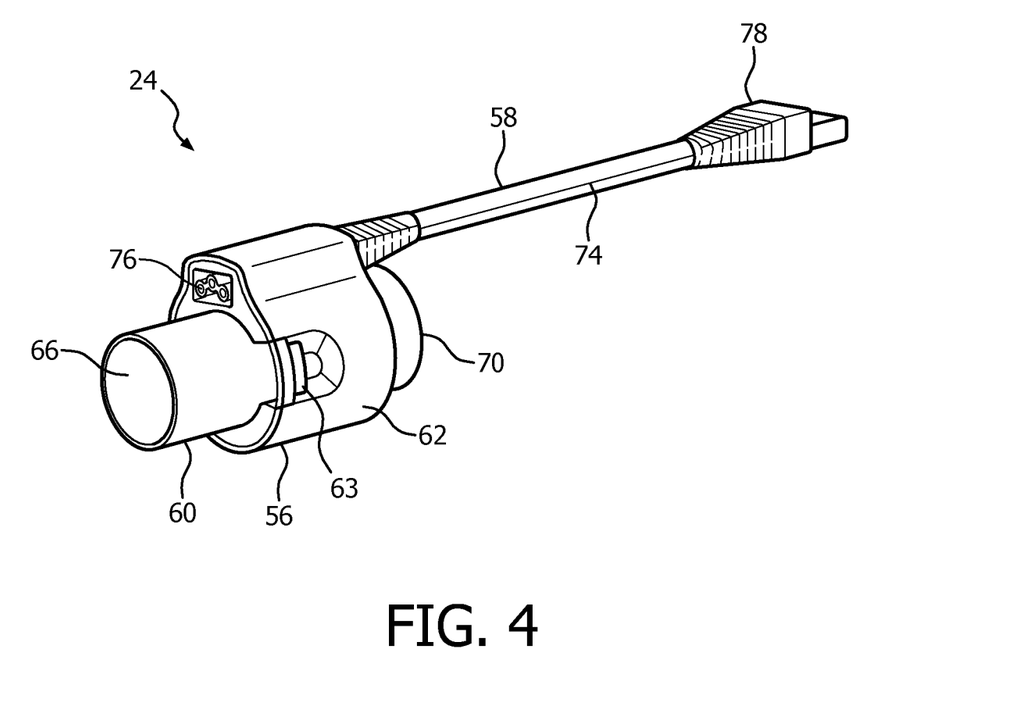
FIG. 4 is an isometric view of an inline accessory adapter forming a part of the system of FIG. 1 according to one exemplary embodiment of the invention.

FIG. 4 is an isometric view of inline accessory adapter 24 according to an exemplary embodiment. As seen in FIG. 4, inline accessory adapter 24 includes a fluid coupling member 56 and a jumper wire harness assembly 58. Fluid coupling member 56 is structured to provide a fluid connection between proximal end 36 of heated tube assembly 22 and inline accessory 7, and jumper wire harness assembly 58 is structured to provide an electrical connection between heating element 46 of heated tube assembly 22 and outlet port 26 of pressure generating device 4.

Figure 5:
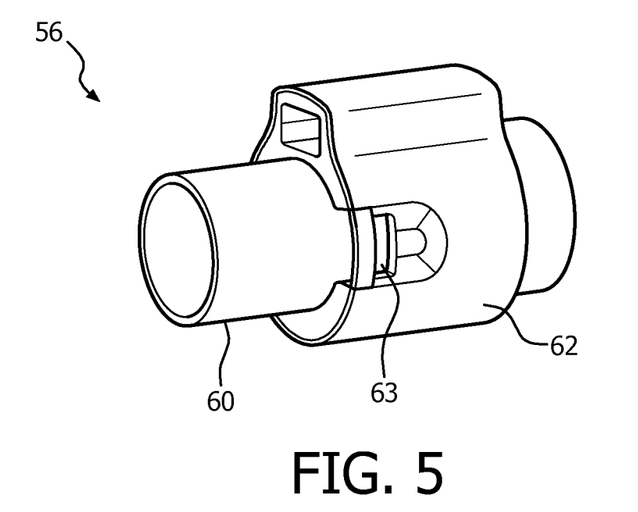
FIG. 5 is an isometric view of a fluid coupling member of the inline accessory adapter of FIG. 4 according to an exemplary embodiment.
Figure 6:
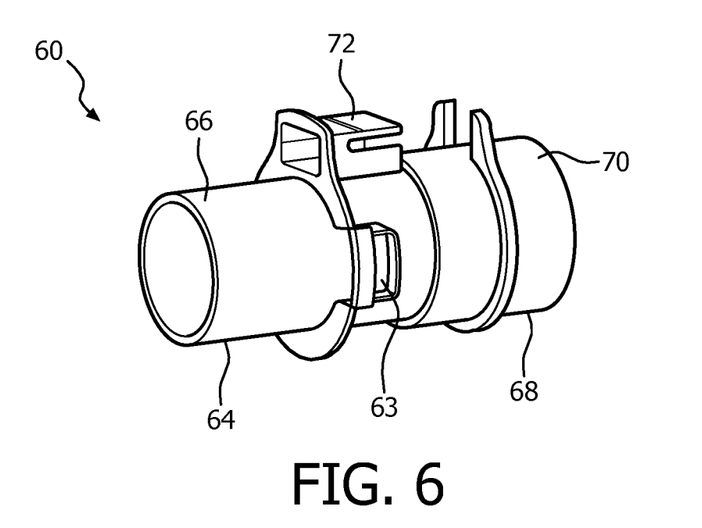
FIG. 6 is an isometric view of a central coupling member of the fluid coupling member of FIG. 5 according to an exemplary embodiment.

FIG. 5 is an isometric view of fluid coupling member 56 according to an exemplary embodiment. Fluid coupling member 56 includes a central coupling member 60 surrounded by a housing member 62. FIG. 6 is an isometric view of central coupling member 60 according to an exemplary embodiment. As seen in FIG. 6, central coupling member 60 includes a first end 64 having a tubular port member 66, which in the illustrated embodiment is a standard male iso conical fitting, and a second end 68 having a tubular port member 70, which in the illustrated embodiment is a standard female iso conical fitting. Central coupling member 60 also includes a connector housing 72 for receiving and holding a connector member of jumper wire harness assembly 58, and slot members 63 for receiving and mating with tab members 53 of heated tube assembly 22.

Figure 7:
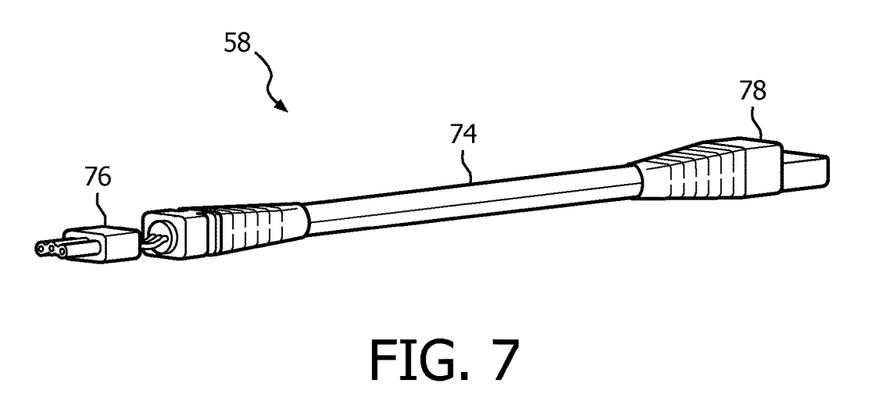
FIG. 7 is an isometric view of a jumper wire harness assembly of the inline accessory adapter of FIG. 4 according to an exemplary embodiment.

FIG. 7 is an isometric view of jumper wire harness assembly 58 according to an exemplary embodiment. Jumper wire harness assembly 58 includes a cable member 74 comprising a number of wires, a first electrical connector 76 provided at a first end of cable member 74, and a second electrical connector 78 provided at a second end of cable member 74. Inline accessory adapter 24 is assembled by inserting the first end of cable member 74 into housing member 62 in a manner wherein first electrical connector 76 is received within connector housing 72 of central coupling member 60.

Having described each of the individual parts of delivery conduit assembly 6, assembly of delivery conduit assembly 6 according to the exemplary embodiment will now be described. First, inline accessory adapter 24 is coupled to proximal end 36 of heated tube assembly 22. More specifically, tubular port member 66 of inline accessory adapter 24 is coupled to tubular port member 50 of heated tube assembly 22 and tab members 53 are inserted into slot member 63. In addition, electrical connector 54 of heated tube assembly 22 is coupled to first electrical connector 76 provided at the first end of cable member 74 of inline accessory adapter 24. Next, the first end of inline accessory 7 is fluidly coupled to tubular port member 70 of inline accessory adapter 24. In the non-limiting exemplary embodiment, inline accessory 7 has a male fitting 9 that is coupled to tubular port member 70. The second end of inline accessory 7 is then fluidly coupled to tubular port member 30 of outlet port 26. In the non-limiting exemplary embodiment, inline accessory 7 has a female fitting 11 that is coupled to tubular port member 30. As will be appreciated, this will result in heated tube assembly 22 being fluidly coupled to outlet port 26 of pressure generating device 4 through inline accessory adapter 24. Finally, second electrical connector 78 provided at the second end of cable member 74 of inline accessory adapter 24 is coupled to electrical connector 34 of outlet port 26. As will be appreciated, this will result in heating element 46 of heated tube assembly 22 being electrically coupled to outlet port 26 of pressure generating device 4 (and thus the power supply of pressure generating device 4) through inline accessory adapter 24.

Thus, inline accessory adapter 24 as just described provides an easy to use a mechanism for enabling the required electrical connection to be made between heated tube capable outlet port 26 and heated tube assembly 22 while simultaneously allowing inline accessory 7 to be inserted into the flow path to the user.

Figure 8:
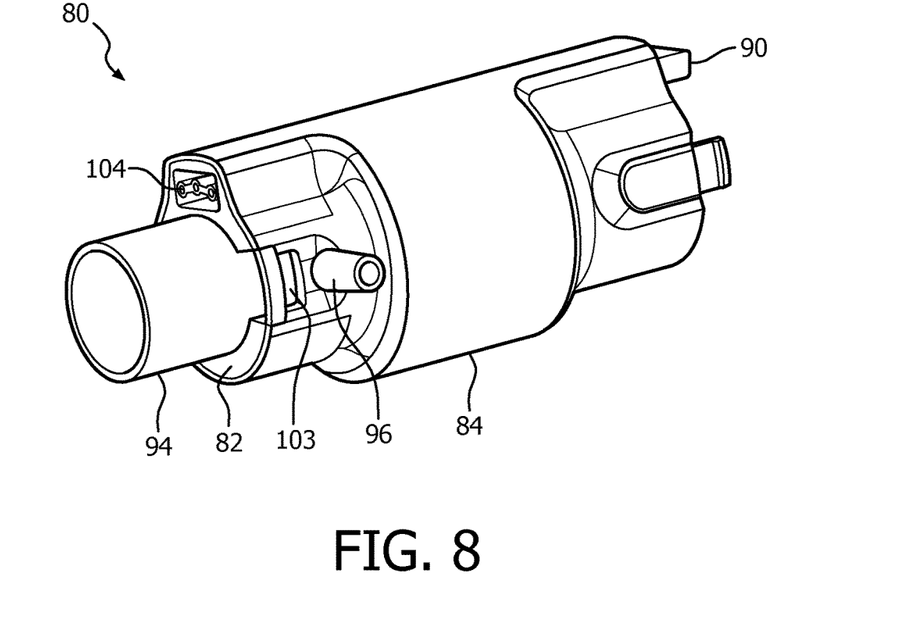
FIG. 8 is an isometric view of an enrichment adapter that may be used in the system of FIG. 1 according to an alternative exemplary embodiment of the present invention.

FIG. 8 is an isometric view of an enrichment adapter 80 according to an alternative exemplary embodiment of the present invention. Enrichment adapter 80 may be substituted for inline accessory adapter 24 and inline accessory 7 in delivery conduit assembly 6 of FIG. 1 to allow oxygen or another supplemental gas to be added to the flow path to patient interface device 8 while at the same time allowing an electrical connection to heated tube assembly 22 from outlet port 26 to be made.

Figure 9:
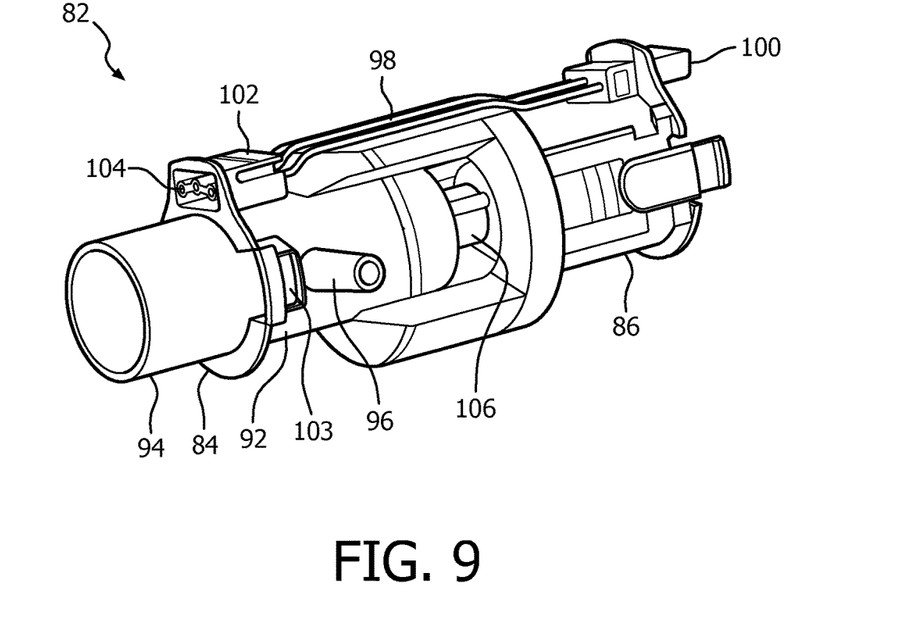
FIGS. 9 and 10 are front and rear isometric views, respectively, of a central adapter assembly forming a part of the enrichment adapter of FIG. 8 according to an exemplary embodiment.
Figure 10:
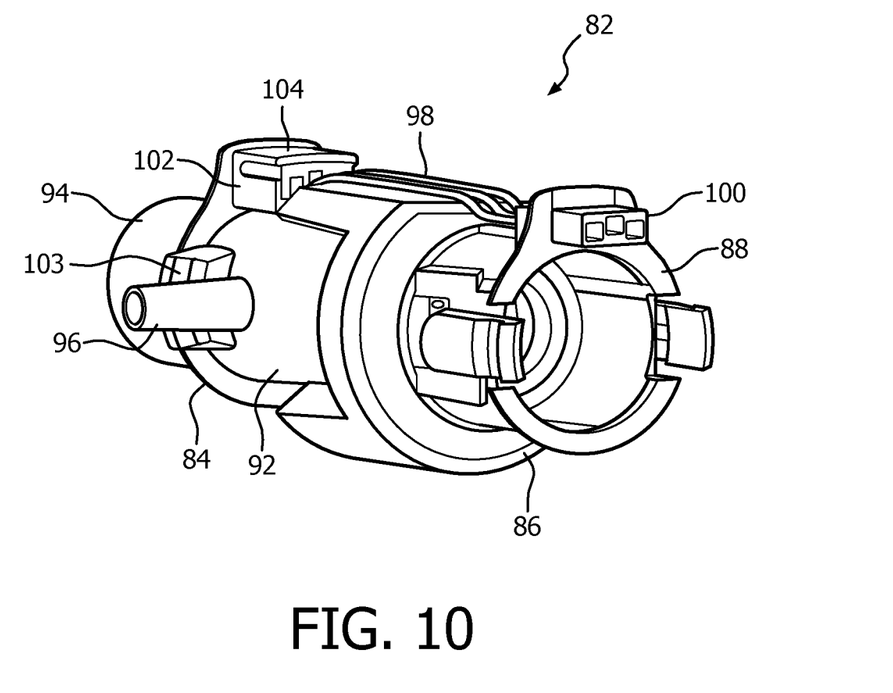

Enrichment adapter 80 includes a central adapter assembly 82 surrounded by a housing member 84. FIGS. 9 and 10 are front and rear isometric views, respectively, of central adapter assembly 82 according to an exemplary embodiment. As seen in FIGS. 9 and 10, central adapter assembly 82 includes a first end 84, a second end 86, and a wire harness assembly 98. Second end 86 is similar in structure to the proximal end 36 of heated tube assembly 22, and includes a tubular port member 88 (which in the illustrated embodiment is a standard female iso conical fitting) and tab members 89 structured to mate with slot members 33 of outlet port 26. As seen in FIGS. 9 and 10 and as described in greater detail below, second end 86 is structured to hold a first electrical connector of 100 of a wire harness assembly 98 to enable second end 86 to be fluidly and electrically coupled to outlet port 26 of pressure generating device 4. First end 84 includes a coupling member 92 that has a tubular port member 94, which in the illustrated embodiment is a standard male iso conical fitting, a gas inlet port 96 providing access to the internal chamber defined by coupling member 92 to allow supplemental gas, such as oxygen, to be introduced into the flow path to patient interface device 8, a connector housing 102 for receiving and holding a second connector member 104 of wire harness assembly 98, and slot members 103 structured to mate with tab members 53 of heated tube assembly. Thus, first end 84 is structured to be fluidly and electrically coupled to the proximal end 36 of heated tube assembly 22. Second end 86 in the illustrated exemplary embodiment further includes a backflow prevention pressure valve 106 structured to prevent the backflow of supplemental gas into pressure generating device 4 when pressure generating device 4 is not operating.

Accordingly, enrichment adapter 80 as just described is a device that may be inserted in between heated tube assembly 22 and outlet port 26 which, when so inserted, simultaneously provides (i) a main fluid path from pressure generating device 4 to heated tube assembly 22, (ii) a secondary path by which supplemental gas may be introduced into the main flow path, and (iii) electrical connection to heated tube assembly 22 from outlet port 26 by way of a jumper in the form of wire harness assembly 98.

Furthermore, while in the illustrated embodiments inline accessory adapter 24 and enrichment adapter 80 are described as being used with heated tube assembly 22, it will be understood that the present invention is not limited to use with only heated tubes. Rather, inline accessory adapter 24 and enrichment adapter 80 may be used with any type of electrical tube assembly to which an electrical connection must be made, such as, without limitation, an electrical tube assembly that includes one or more wires for carrying an electrical signal from a patient interface device to a base unit and/or from a base unit to a patient interface device.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An adapter apparatus for a respiratory therapy system having a pressure generating device and an electrical tube assembly coupled to a patient interface device, the pressure generating device including an outlet port having a first housing having a first mating member structured to be mated with a second mating member of the electrical tube assembly to allow the electrical tube assembly to be connected to the first housing, the adapter apparatus comprising:
   a first end having a first port member structured to be fluidly coupled to the electrical tube assembly;
   a second end having a second port member structured to receive a flow of breathing gas generated by the pressure generating device, the adapter apparatus being structured to deliver the flow of breathing gas to the electrical tube assembly through the first port member;
   a wire assembly having a first electrical connector structured to be electrically coupled to the electrical tube assembly and a second electrical connector structured to be electrically coupled to the pressure generating device in order to provide an electrical connection between the electrical tube assembly and the pressure generating device;
   a third mating member having a configuration that matches a configuration of the first mating member, the third mating member being structured to be mated with the second mating member of the electrical tube assembly to allow the electrical tube assembly to be connected to the adapter apparatus; and
   a connector housing, wherein the first electrical connector is received and held within the connector housing, wherein the first port member, the second port member and the connector housing are provided as part of a fluid coupling member, and wherein the fluid coupling member includes a housing that covers the connector housing and receives and holds at least a portion of the wire assembly.

2. The adapter apparatus according to claim 1, further comprising an inline accessory device having a first end fluidly coupled to the second port member and a second end structured to receive the flow of breathing gas generated by the pressure generating device, wherein the wire assembly extends along a length of the inline accessory device.

3. The adapter apparatus according to claim 1, wherein the first port member is provided as part of a coupling member having an internal chamber, wherein the coupling member has a gas inlet port providing access to the internal chamber to allow a supplemental gas to be introduced into the internal chamber.

4. The adapter apparatus according to claim 3, wherein the second end is coupled to the coupling member, wherein the second electrical connector is structured to be electrically coupled to an outlet port of the pressure generating device, and wherein the second port member is structured to be fluidly coupled to the outlet port of the pressure generating device.

5. The adapter apparatus according to claim 3, wherein the second end includes a backflow prevention pressure valve.

6. The adapter apparatus according to claim 1, wherein the first mating member is a first slot member, the second mating member is a second tab member, and the third mating member is a third slot member.

7. A respiratory therapy system, comprising:
   a pressure generating device structured to generate a flow of breathing gas, the pressure generating device including an outlet port having a first housing having a first electrical connector and a first mating member;
   a patient interface device;
   an electrical tube assembly coupled to the patient interface device at a distal end thereof, the electrical tube assembly having a second housing provided at a proximal end thereof, the second housing having a second electrical connector and a second mating member, wherein the second electrical connector is structured to be coupled to the first electrical connector to allow power and/or control signals to be provided to the electrical tube assembly from the pressure generating device and wherein the second mating member is structured to be mated with the first mating member to allow the second housing to be connected to the first housing; and
   an adapter apparatus provided between the pressure generating device and the electrical tube assembly, the adapter apparatus including:
      a first end having a first port member fluidly coupled to the electrical tube assembly;
      a second end having a second port member structured to receive the flow of breathing gas, the adapter apparatus being structured to deliver the flow of breathing gas to the electrical tube assembly through the first port member;
      a wire assembly having a third electrical connector electrically coupled to the second electrical connector of the electrical tube assembly and a fourth electrical connector electrically coupled to the first electrical connector of the pressure generating device to thereby provide an electrical connection between the electrical tube assembly and the pressure generating device; and
      a third mating member having a configuration that matches a configuration of the first mating member, the third mating member being mated with the second mating member of the electrical tube assembly to connect the second housing to the adapter apparatus, wherein the adapter apparatus further comprises a connector housing, wherein the third electrical connector is received and held within the connector housing, and wherein the first port member, the second port member and the connector housing are provided as part of a fluid coupling member, and wherein the fluid coupling member includes a housing that covers the connector housing and receives and holds at least a portion of the wire assembly.

8. The respiratory therapy system according to claim 7, further comprising an inline accessory device having a first end fluidly coupled to the second port member and a second end fluidly coupled to the pressure generating device, wherein the wire assembly extends along a length of the inline accessory device.

9. The respiratory therapy system according to claim 8, wherein the inline accessory device comprises an oxygen enrichment adapter, a pressure valve or a bacteria filter.

10. The respiratory therapy system according to claim 7, wherein the first port member is provided as part of a coupling member having an internal chamber, wherein the coupling member has a gas inlet port providing access to the internal chamber to allow a supplemental gas to be introduced into the internal chamber.

11. The respiratory therapy system according to claim 10, wherein the second end of the adapter apparatus is coupled to the coupling member, and wherein the second port member is fluidly coupled to the outlet port of the pressure generating device.

12. The respiratory therapy system according to claim 11, wherein the second end includes a backflow prevention pressure valve.

13. The respiratory therapy system according to claim 11, wherein the first mating member is a first slot member, the second mating member is a second tab member, and the third mating member is a third slot member.

* * * * *